United States Patent [19]
Jenkins

[11] Patent Number: 5,700,249
[45] Date of Patent: Dec. 23, 1997

[54] NEEDLE POINT PROTECTOR

[76] Inventor: David Howell Jenkins, 1 Langton Place, Charlton Kings, Cheltenham, Gls., United Kingdom, GL51 8HW

[21] Appl. No.: 628,619

[22] PCT Filed: Oct. 31, 1994

[86] PCT No.: PCT/GB94/02372

§ 371 Date: Apr. 9, 1996

§ 102(e) Date: Apr. 9, 1996

[87] PCT Pub. No.: WO95/12426

PCT Pub. Date: May 11, 1995

[30] Foreign Application Priority Data

Nov. 4, 1993 [GB] United Kingdom ............... 9322786
Jul. 27, 1994 [GB] United Kingdom ............... 9415157

[51] Int. Cl.⁶ .................................................. A61M 5/00
[52] U.S. Cl. ...................................... 604/263; 604/192
[58] Field of Search ............................. 604/263, 192, 604/187, 110, 198

[56] References Cited

U.S. PATENT DOCUMENTS 4,139,009  2/1979  Alvarez .
4,735,618  4/1988  Hagen .
4,790,828  12/1988  Dombrowski et al. .
4,911,706  3/1990  Levitt .
5,053,017  10/1991  Chamuel .

FOREIGN PATENT DOCUMENTS 0 321 903   6/1989   European Pat. Off. .
0 344 606   12/1989  European Pat. Off. .
  328864    5/1930   United Kingdom .
1 506 572   4/1978   United Kingdom .
2 202 446   9/1988   United Kingdom .
2 252 046   7/1992   United Kingdom .
WO 88/0873  10/1988  WIPO .

Primary Examiner—John D. Yasko
Attorney, Agent, or Firm—Young & Thompson

[57] ABSTRACT

The protector comprises a protective element, e.g. a cap (16), movable in use along the implement between an inoperative position in which it exposes the pointed end or sharp edge portion of the implement and an operative position (FIG. 3) in which it covers the pointed end or sharp edge portion of the implement. The protector also comprises a holder (15) for fitting to the implement and a device, e.g. arm (17), connecting the protective element to the holder to in use allow the protective element to move along the implement between the inoperative and operative positions but to prevent separation of the protective element from the implement. In a preferred embodiment, the protective element flips into a tilted position to prevent unintentional movement of the protective element from its operative to its inoperative positions.

7 Claims, 2 Drawing Sheets

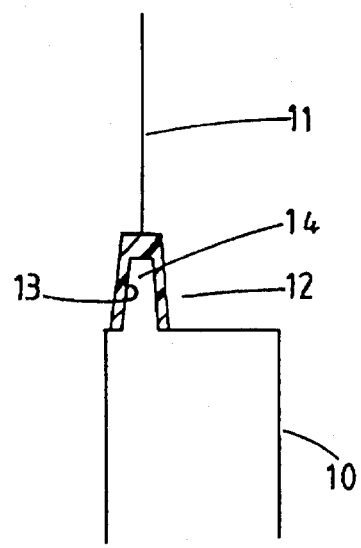
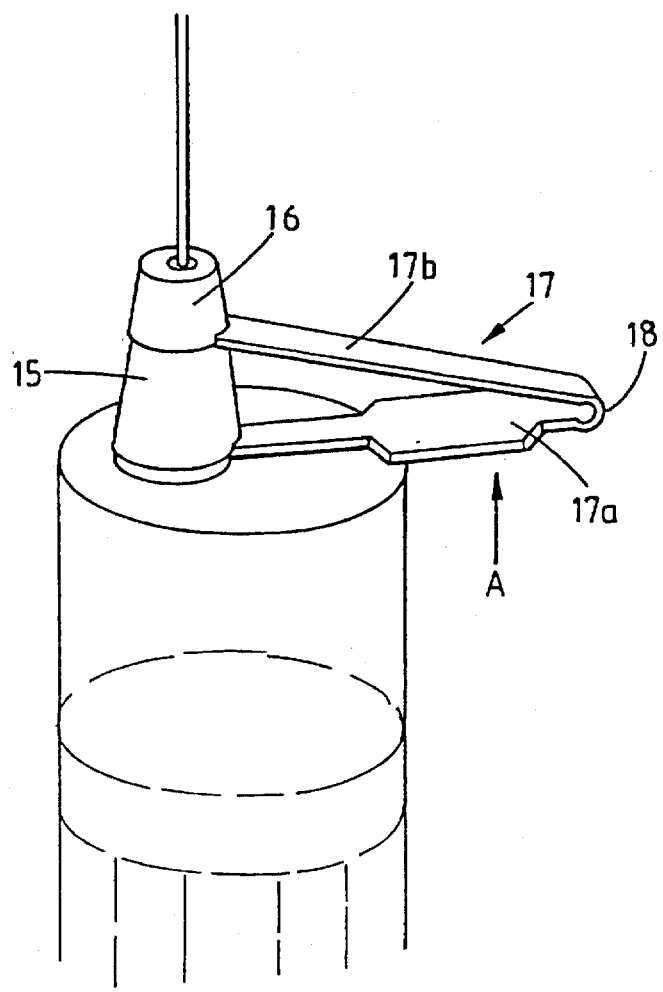
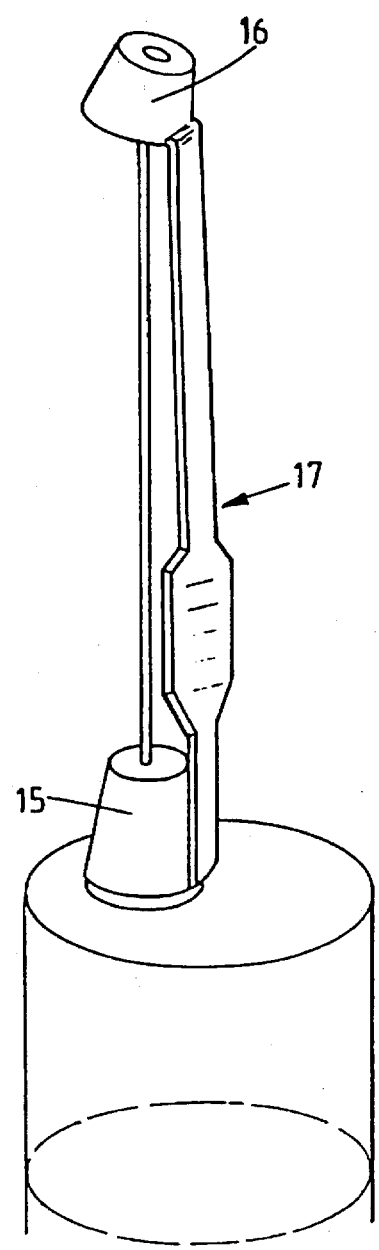
FIG.1
FIG.2
FIG.3

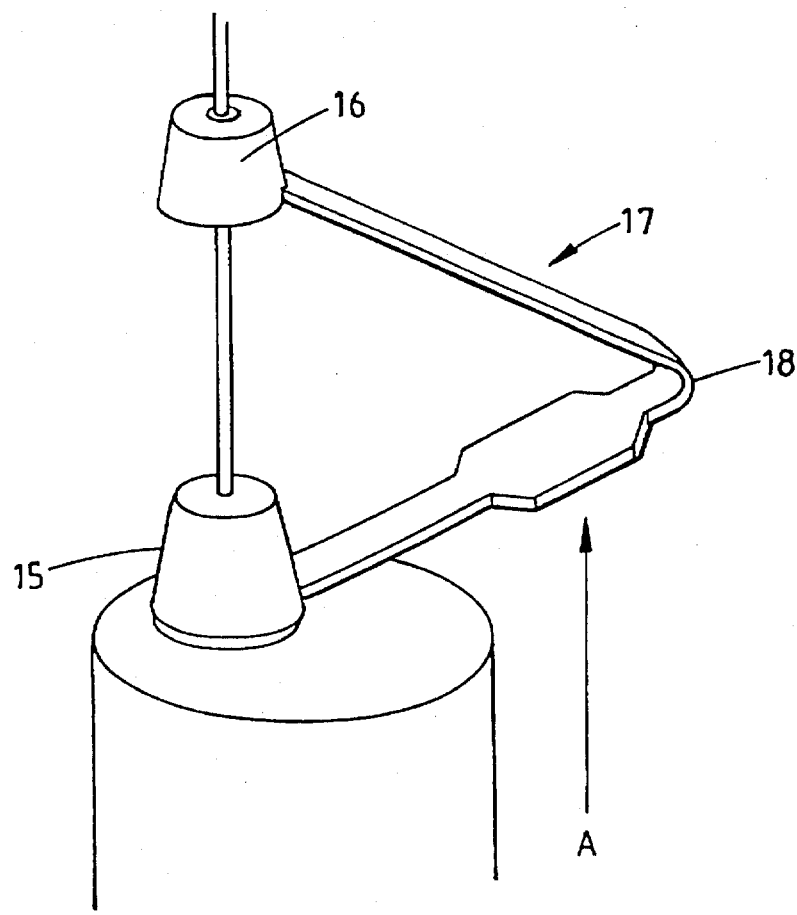
FIG.4.
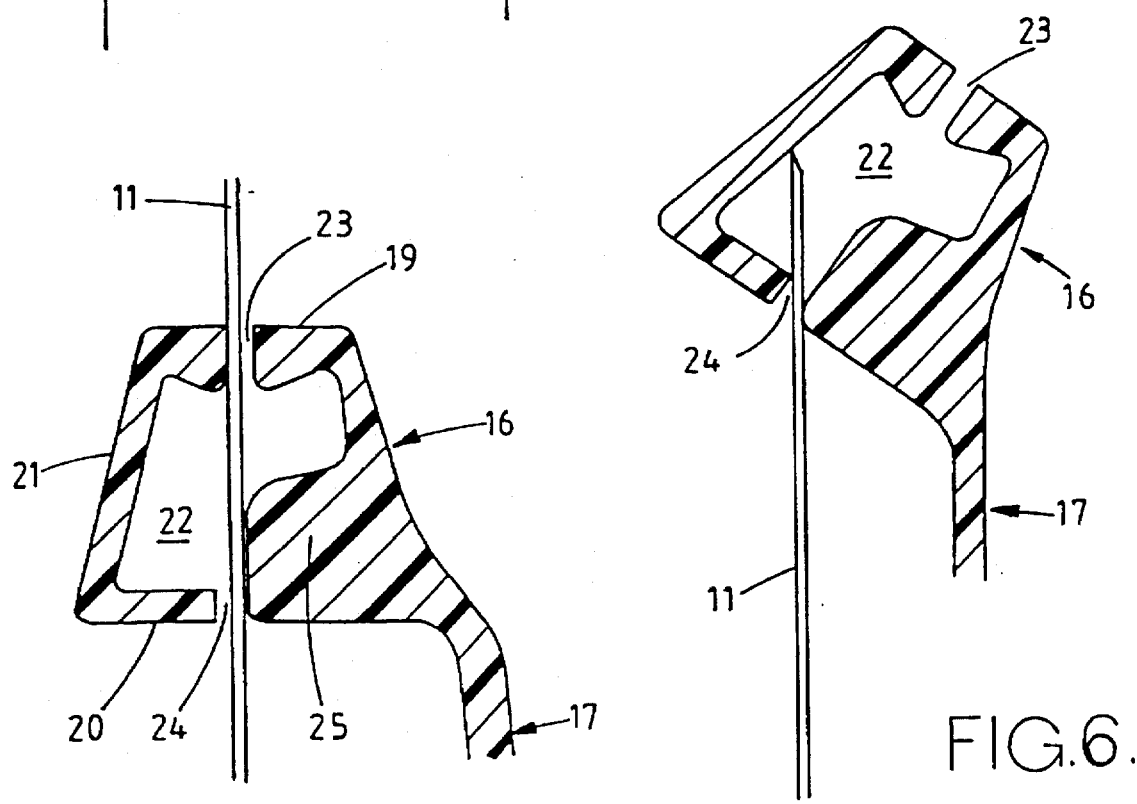
FIG.5.
FIG.6.

NEEDLE POINT PROTECTOR

FIELD OF THE INVENTION

This invention relates to a needle point protector particularly for a hypodermic syringe.

BACKGROUND OF THE INVENTION

Hypodermic syringes have many uses ranging from the delivery of chemical substances and medicamentation, to the removal of body fluid, typically although not exclusively blood products, and laboratory use. Such use is characterised by the needle point being exposed for the procedure to be effected. Following this procedure, it is desirable for the needle point to be resheathed/covered to prevent it coming into contact with another person by design or accident, and or during the disposal procedure. There is a need for the safe resheathing/covering of the needle point.

EP-A-321903 discloses a needle point protector comprising a protective element movable along the needle between an operative position in which it exposes the pointed end of the needle and an operative position in which it covers the pointed end of the needle, a holder which can be fixed to the needle at a position remote from the pointed end of the needle and a single elongate arm connecting the holder to the protective element. The arm is connected to the holder and to the protective element through respective hinges and the arm also has a further hinge intermediate its ends. When in an inoperative position the arm extends generally parallel to the needle and in order to move the protective element to its operative position, it is necessary to pull down the arm to a position in which it extends transversely to the needle. This will take a user's fingers unacceptably close to the needle tip.

U.S. Pat. No. 4,911,706 also discloses a needle point protector comprising a protective element, a holder and a single arm between the protective element and the holder. This arm is formed of resilient spring-like plastics material and is held in a folded condition by a latch assembly. With time the resilient arm will relax. The force exerted by the arm when unlatched will depend upon the time over which the needle protector has been stored and the protective cap may not move over the point of the needle.

SUMMARY OF THE INVENTION

According to one aspect of to the present invention there is provided a needle point protector comprising a protective element movable along the needle from an inoperative position in which it exposes the pointed end of the needle to an operative position in which it covers the pointed end of the needle, a holder which can be fixed with respect to the needle at a position remote from the pointed end of the needle, and a single elongate arm connecting the protective element to the holder, the protective element having an internal cavity in which the pointed end of the needle is disposed when in use the protective element is in its operative position and an aperture through which the pointed end of the needle can pass in order to move into said internal cavity as the protective element is moved from its inoperative to its operative position, the single elongate arm having a hinge intermediate its ends and being movable from a folded condition in which the arm extends in use transversely to the longitudinal extent of the needle and in which the protective cap is in its inoperative position to an extended condition in which the protective cap is moved to its operative position by applying manual pressure to the part of the arm between the holder and the hinge, and the elongate arm being connected to the protective cap in such a way that when in use the protective cap is moved to its operative position the angle between the protective cap and the elongate arm changes and stores energy so that when the pointed end of the needle passes into the cavity the protective cap flips into a tilted position as some of the stored energy is released and the aperture is moved out of alignment with the pointed end of the needle.

Conveniently, the protective element is internally shaped so as to encourage the protective element to tilt as in use the pointed end of the needle passes into the cavity so that the aperture is moved out of alignment with the pointed end of the needle.

Conveniently, the protector is formed as an integral plastics moulding, typically in polypropylene.

According to another aspect of the invention there is provided a needle point protector comprising a protective element movable along the needle from an inoperative position in which it exposes the pointed end of the needle to an operative position in which it covers the pointed end of the needle, a holder which can be fixed with respect to the needle at a position remote from the pointed end of the needle, and a single elongate arm connecting the protective element to the holder, the protective element having an internal cavity in which the pointed end of the needle is disposed when in use the protective element is in its operative position and an aperture through which the pointed end of the needle can pass in order to move into said internal cavity as the protective element is moved from its inoperative to its operative position, the single elongate arm having a hinge intermediate its ends and being manually movable from a folded condition in which the arm is constrained to extend in use transversely to the longitudinal extent of the needle and in which the protective cap is in its inoperative position to an extended condition in which the protective cap is moved to its operative position by applying manual pressure to the part of the arm between the holder and the hinge.

The invention also provides a hypodermic syringe equipped with a protector as described above.

BRIEF DESCRIPTION OF THE DRAWINGS

The invention will now be more particularly described, by way of example, with reference to the accompanying drawings, in which:

FIG. 1 shows a conventional syringe and needle fitting;

FIG. 2 shows one embodiment of a protector according to the invention mounted on a hypodermic syringe in an inoperative position;

FIG. 3 shows the protector of FIG. 2 in an operative position;

FIG. 4 shows the protector of FIGS. 2 and 3 in a position intermediate its inoperative and operative positions;

FIG. 5 is a cross-sectional view of the protective element in the position shown in FIG. 4; and FIG. 6 is a cross-sectional view of the protective element in the position shown in FIG. 3.

DESCRIPTION OF THE PREFERRED EMBODIMENTS

FIG. 1 of the drawings shows a conventional syringe. The syringe comprises a syringe body 10, a needle 11 and a needle holder 12. The holder 12 is of frusto-conical shape and has a frusto-conical cavity 13 for receiving a complementary projection 14 on the syringe body 10. The holder may be internally threaded for engagement with an external thread on the projection 14 or may be otherwise secured to the projection 14, such as by adhesive or as a snap or push fit. The needle 11 is secured to the holder 12, such as by moulding it to the needle 11.

Referring now to FIGS. 2 to 6 of the accompanying drawings, there is shown therein a protector comprising holder 15 (similar to holder 12), a protective cap 16 and an arm 17 connecting the cap 16 to the holder 15. The arm 17 is formed in two parts 17a and 17b with a hinged joint 18 therebetween.

The cap 16 is of frusto-conical external shape and comprises a top wall 19, a bottom wall 20 of larger diameter than the top wall and a skirt 21. The cap 16 has an internal cavity 22 and the top and bottom walls 19 and 20, respectively, have aligned apertures 23 and 24, respectively, which communicate with the internal cavity 22.

The protector is formed as a plastics moulding, typically in polypropylene, and is moulded in its inoperative position (see FIG. 2) so that as the arm 17 is extended the angle between the protective cap 16 and the arm 17 changes and stores energy. This has the advantage that when the pointed end of the needle 11 enters the cavity 22 (as described hereinafter) the cap 16 flips into a tilted position (see FIG. 6) as some of the stored energy is released.

In the example shown, the internal cavity 22 is of asymmetrical shape, the asymmetry of the cavity being caused by a bulbous protrusion 25 extending into the cavity between the bottom wall 20 and the skirt 21 on that side of the aperture 24 adjacent to the arm 17. The purpose of this protrusion 25 is to further encourage the cap 16 to flip into the tilted position shown in FIG. 6 when the point of the needle 11 enters the cavity 22. It also has the advantage that it provides a nice feel to the flipping action leaving the user with no doubt that the cap 22 has moved to a safe position. However, it is difficult to mould an internal cavity of this shape and in practice the cap 22 would have to be moulded in two parts which are then secured together such as by ultrasonic welding. This, of course, adds to the cost of the protector. The protrusion 25 may, therefore, be omitted. This would create more space to accommodate any blood on the needle 11.

FIG. 2 shows the protector in an inoperative position with the cap 16 mounted about the needle 11 and bearing against the holder 15. When the syringe has been used, the protective cap 16 can be placed over the needle point by extending the arm 17. This is achieved by applying pressure to the lower arm portion 17a in the direction indicated by arrow A in FIG. 2. The two arm portions 17a and 17b will unfold as shown in FIG. 4 and the cap 16 will move along the longitudinal extent of the needle until the needle point passes into the cavity 22 of the cap 16 as shown in FIGS. 3 and 6. When the point of the needle 11 leaves the aperture 23 and passes into the cavity 22, the cap 16 flips into the tilted position shown in FIG. 6.

Once the cap has flipped into this tilted position, it is virtually impossible for the needle tip to be reinserted into the aperture 23 unintentionally and the cap will prevent the needle tip from accidental contact with humans.

Ideally, the aperture 23 is large enough to allow any blood on the needle 11 to be carried into the cavity 22 but small enough to prevent blood seeping therefrom.

The embodiment described above is given by way of example only and various modifications will be apparent to persons skilled in the art without departing from the scope of the invention as defined in the appended claims.

For example, it is conceivable that the aperture 23 could be made self-sealing, although, in practice, this is unlikely as it would add to the cost and prevent any blood on the needle 11 being carried into the cavity 22.

Also, if the cap 16 is made of a sufficiently hard plastics material, e.g. polycarbonate, or is made of, or lined with metal, the cap could crush or bend the needle as it moves into position over the needle point. This would render the needle unreusable.

The arm 17 could be connected to the end of the cap 16 provided with hole 23 instead of the end of the cap 16 provided with hole 24. In this case, the cap 16 would tilt in an opposite direction. It will also be less compact when in an inoperative position. However, it could reduce any risk there may be of the cap 16 jamming against the needle holder 12.

I claim:

1. A needle point protector comprising a protective element (16) movable along the needle (11) from an inoperative position in which it exposes the pointed end of the needle to an operative position in which it covers the pointed end of the needle, a holder (15) which can be fixed with respect to the needle at a position remote from the pointed end of the needle, and a single elongate arm (17) connecting the protective element to the holder, the protective element having an internal cavity (22) in which the pointed end of the needle is disposed when in use the protective element is in its operative position and an aperture (23) through which the pointed end of the needle can pass in order to move into said internal cavity as the protective element is moved from its inoperative to its operative position, the single elongate arm having a hinge intermediate (18) its ends and being movable from a folded condition in which the arm extends in use transversely to the longitudinal extent of the needle and in which the protective cap is in its inoperative position to an extended condition in which the protective cap is moved to its operative position by applying manual pressure to the part of the arm between the holder and the hinge, and the elongate arm being connected to the protective cap in such a way that when in use the protective cap is moved to its operative position the angle between the protective cap and the elongate arm changes and stores energy so that when the pointed end of the needle passes into the cavity the protective cap flips into a tilted position as some of the stored energy is released and the aperture is moved out of alignment with the pointed end of the needle.

2. A needle point protector as claimed in claim 1, wherein the protective element (16) is internally shaped so as to encourage the protective element to tilt as in use the point needle passes into the cavity (22) so that the aperture (23) is moved out of alignment with the pointed end of the needle.

3. A needle point protector as claimed in claim 2, wherein the internal cavity (22) is of asymmetrical shape.

4. A needle point protector as claimed in claim 1, wherein the part of the arm between the holder and the hinge has a thumb push portion which is wider than the remainder of the arm.

5. A needle point protector comprising a protective element (16) movable along the needle (11) from an inoperative position in which it exposes the pointed end of the needle to an operative position in which it covers the pointed end of the needle, a holder (15) which can be fixed with respect to the needle at a position remote from the pointed end of the needle, and a single elongate arm (17) connecting the protective element to the holder, the protective element having an internal cavity (22) in which the pointed end of the needle is disposed when in use the protective element is in its operative position and an aperture (23) through which the pointed end of the needle can pass in order to move into said internal cavity as the protective element is moved from its inoperative to its operative position, the single elongate arm having a hinge intermediate (18) its ends and being movable from a folded condition in which the arm extends in use transversely to the longitudinal extent of the needle and in which the protective cap is in its inoperative position to an extended condition in which the protective cap is moved to its operative position by applying manual pressure to the part of the arm between the holder and the hinge.

6. A hypodermic syringe equipped with a protector as claimed in claim 1.

7. A hypodermic syringe equipped with a protector as claimed in claim 5.

* * * * *